United States Patent

Randive et al.

[11] Patent Number: 6,162,418
[45] Date of Patent: *Dec. 19, 2000

[54] NON-STRINGY TOOTHPASTE

[75] Inventors: Vinayak Bhalchandra Randive, Maharashtra; Vijay Kamalakant Gadkari, Bombay, both of India

[73] Assignee: FMC Corporation, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 09/071,945

[22] Filed: May 4, 1998

[51] Int. Cl.[7] ..................................................... A61K 7/16
[52] U.S. Cl. ................................................................ 424/49
[58] Field of Search ........................................ 424/49–58

[56] References Cited

U.S. PATENT DOCUMENTS

| | | | |
|---|---|---|---|
| 4,029,760 | 6/1977 | De Roeck | 424/49 |
| 4,457,908 | 7/1984 | Scott | 424/49 |
| 4,565,692 | 1/1986 | Mulvey et al. | 424/49 |
| 4,604,280 | 8/1986 | Scott | 424/49 |
| 4,645,662 | 2/1987 | Nakashima | 424/52 |
| 4,702,905 | 10/1987 | Mitchell | 424/49 |
| 4,894,220 | 1/1990 | Nabi et al. | 424/49 |
| 5,002,934 | 3/1991 | Norton et al. | 424/49 |
| 5,094,839 | 3/1992 | Lowder et al. | 424/49 |
| 5,236,696 | 8/1993 | Catiis et al. | 424/49 |
| 5,296,214 | 3/1994 | Gaffar | 424/49 |
| 5,468,189 | 11/1995 | Sakuma et al. | 424/49 |
| 5,496,541 | 3/1996 | Cutler | 424/49 |
| 5,531,982 | 7/1996 | Gaffar | 424/49 |
| 5,582,816 | 12/1996 | Mandanas et al. | 424/49 |
| 5,788,951 | 8/1998 | Blake-Haskins | 424/49 |

*Primary Examiner*—Shep K. Rose
*Attorney, Agent, or Firm*—Bradley A. Swope; Robert L. Andersen; I. Robert Silverman

[57] ABSTRACT

Described herein is a toothpaste composition which comprises an orally acceptable vehicle, a polishing agent, a surface active agent and a binder, the binder containing kappa carrageenan and a cellulose gum, the percent by weight concentration of binder being in the range of about 0.30 to 0.80%, and the ratio of kappa carrageenan to cellulose gum being in the range of about 25:75 to 75:25. A preferred concentration of binder is in the range of about 0.45 to 0.65 and a preferred ratio of kappa carrageenan to cellulose gum is in the range of about 55:45 to 75:25. The toothpaste is surprisingly non-stringy, exhibits good consistency, transparency and physical stability.

8 Claims, No Drawings

NON-STRINGY TOOTHPASTE

This invention relates to a gel toothpaste comprising kappa carrageenan and a cellulose gum. In particular, it relates to a gel toothpaste comprising a binder containing kappa carrageenan and a cellulose gum such as carboxymethylcellulose in a formulation so as to provide a toothpaste having low stringiness. The toothpaste has good consistency and maintains good physical stability at relatively low concentrations of binder.

BACKGROUND

For toothpaste manufacturers, the stringiness of the toothpaste ribbon has historically been and is today an important parameter of concern. High volume manufacturers typically package toothpaste in laminated tubes using high speed filling lines that are capable of filling 80 to 200 tubes per minute. To meet the demands of such production, it is important that the toothpaste ribbon cuts off sharply from the tube. If toothpaste remains in the sealing portion of the lamitube, tube sealing could be faulty resulting in the opening of the tube. Also, toothpaste string coming out of the tube could cause blackening on the outside portion of the tube in the sealing area due to burning while it is being sealed. Open and blackened tubes are rejected during production. On the consumer side, stringy toothpaste gives a shabby look to the toothpaste nozzle during usage. These problems are inherent with a toothpaste that tails or is stringy. To avoid or minimize these problems, a toothpaste formulation is desired that provides a sharp cut off, i.e., a toothpaste that is not stringy or does not tail.

Toothpaste generally contains a polishing agent or abrasive, humectant, thickener or binder, water, foaming agent and flavoring agents. The humectant and water are also referred to collectively as the vehicle. In addition, agents that provide therapeutic or cosmetic benefits may be incorporated such as fluoride and tartar control agents. In seeking to provide a non-stringy toothpaste, the formulation must maintain other excellent physical properties to which the consumer is accustomed. For consumer satisfaction these properties should provide a toothpaste that has appealing taste, good cleansing effect, is easy to rinse, excellent mouth feel, and chemical and physical stability. Furthermore, these properties should be provided in a toothpaste that is cost effective for the consumer.

The formulation properties of a toothpaste will depend on the inherent properties of the binder, abrasive, humectant, water and other components of the formulation, and they will also depend on how these components behave in complex mixtures with each other. In general, stringiness will be a function of the type and amount of binder and abrasive used in the toothpaste formulation. To a lesser extent, stringiness will also be effected by the choice of humectant. Among the commonly used binders, for example, carboxymethylcellulose (CMC) is known to generally promote stringiness while carrageenan reduces stringiness. Among the commonly used abrasives, silica generally enhances stringiness relative to chalk and dicalcium phosphate (DCP).

The generic term carrageenan is applied to dozens of similar polysaccharides derived from seaweed. All carrageenans contain repeating galactose units joined by alternating $\beta 1 \rightarrow 3$ and $\alpha 1 \rightarrow 4$ glycosidic linkages and are partially sulfated. The types of carrageenans may be distinguished, in part, by their degree of sulfation. Kappa carrageenan has a repeating unit of D-galactose-4-sulfate-3,6-anhydro-D-galactose providing a sulfate ester content of about 18 to 25%. Iota carrageenan has a repeating unit of D-galactose-4-sulfate-3,6-anhydro-D-galactose-2-sulfate providing a sulfate ester content of about 25 to 34%. Lambda carrageenan has a repeating unit of D-galactose-2-sulfate-D-galactose-2,6-disulfate providing a sulfate ester content of about 30 to 40%.

The carrageenans forms gels that are thixotropic. Such gels are reported to exhibit excellent extrudability, flavor release and rinsability. The use of kappa and iota carrageenan as binders in gel toothpaste is known to also provide a toothpaste that is non-stringy. However, as U.S. Pat. No. 4,604,280 notes a problem associated with compositions made using carrageenan is that the thickness or viscosity of the composition tends to decrease when the composition is subjected to mechanical working at a temperature below the gel-sol temperature. For carrageenan, the gel-sol temperature is in the range of about 450 to 49° C. Sometimes a minor working below this temperature can cause a substantial decrease in viscosity. To compensate for such loss of viscosity, it is often necessary to employ additional amounts of carrageenan to the formulation than would otherwise be necessary. Carrageenan is therefore often employed at a weight concentration in excess of one percent.

Of the types of carrageenan, iota, kappa and lambda, that have been used in toothpaste formulations, iota carrageenan is usually preferred. This preference is due in part to a difference in hardening effect. Relative to gels based on iota carrageenan, gels based on kappa carrageenan are reported to harden more readily on the shelf. Toothpastes that harden in such a manner become difficult to squeeze from the tube. Also, relative to the iota form, gels based on kappa carrageenan are more likely to have a syneresis problem; i.e., they will be more likely to have water separate from the gel. Toothpaste products are deemed unacceptable if they are not stable against such phase separation. For these reasons, when carrageenan is employed as a binder in gel toothpaste it is usually the iota form that is chosen.

It is an objective of this invention to provide a non-stringy gel toothpaste which is comprised of kappa carrageenan as a major component of the binder but without the aforementioned stability problems associated with kappa carrageenan. It is a further objective to provide such a toothpaste where the concentration of kappa carrageenan is relatively low.

SUMMARY OF THE INVENTION

It has now been found that a binder containing kappa carrageenan and a cellulose gum in toothpaste formulations provides a toothpaste that is surprisingly non-stringy and exhibits good consistency and physical stability. The toothpaste may also be formulated to have excellent transparency. The concentration by weight of binder in the formulation is in the range of about 0.30 to 0.80%. The weight ratio of kappa carrageenan to cellulose gum in the binder is in the range of about 25:75 to 75:25. A preferred concentration of binder is in the range of about 0.45 to 0.65 and a preferred ratio of kappa carrageenan to cellulose gum is in the range of about 55:45 to 75:25. A preferred cellulose gum is carboxymethylcellulose (CMC).

DETAILED DESCRIPTION OF THE INVENTION

This invention pertains to a toothpaste comprised of a binder containing kappa carrageenan and a cellulose gum in a formulation that is non-stringy, has good consistency, transparency and exhibits good physical stability. The invention overcomes the problem of stringiness that is associated with cellulose gums such as carboxymethylcellulose or CMC and the problems of syneresis and stability that are associated with kappa carrageenan. The binder obtained by mixing the cellulose gum and kappa carrageenan may be used in a standard gel toothpaste formulation to provide a toothpaste that is non-stringy, is stable to water and flavor separation over extended periods of time, has good Cuban values (has a good consistency) and does not appreciably harden over extended time periods. The binder is useful at relatively low concentrations which is important as a cost consideration.

This invention provides a toothpaste composition which comprises an orally acceptable vehicle, a polishing agent, a surface active agent and a binder, the binder containing kappa carrageenan and a cellulose gum, the percent by weight concentration of binder being in the range of about 0.30 to 0.80%, and the ratio of kappa carrageenan to cellulose gum being in the range of about 25:75 to 75:25. Important features of this invention are (a) the percent by weight concentration of the binder and (b) the weight ratio of kappa carrageenan to cellulose gum in the binder. A preferred concentration of binder is in the range of about 0.45 to 0.65%. A more preferred concentration of binder is between about 0.45 to 0.61%. A preferred ratio of kappa carrageenan to cellulose gum is in the range of about 55:45 to 75:25. A more preferred ratio is between about 60:40 to 75:25, and a still more preferred ratio is between about 62:38 to 71:29. The cellulose gum and kappa carrageenan in the binder may be in the form of a dry blend mixture or a coprocessed mixture, either of which are suitable. Such mixtures may be prepared according to methods that are generally known in the art.

Cellulose gums that may be used with this invention include those that are generally suitable as gum thickeners in toothpaste. Examples of such gums are hydroxyethylcellulose, hydroxypropylcellulose, and carboxymethylcellulose. As used herein, the term "cellulose gum" refers to any one or a combination of cellulose gums. A preferred gum is carboxymethylcellulose.

Toothpastes normally comprise a vehicle, a polishing agent, a binder and a surface active or detersive agent. In addition, agents that provide therapeutic or cosmetic benefits may be incorporated such as an enamel hardening agent, a tartar control agent, a whitening agent, and an antibacterial agent. One or more sweeteners and flavoring agents are optionally added for consumer satisfaction. Titanium dioxide may also be added as an opacifier or a whitening agent where such is desired.

The vehicles of this toothpaste are orally acceptable vehicles comprised of water and a humectant, such as polyols of three to six carbons where each carbon is hydroxylated, and mixtures thereof. Examples of humectants include glycerol, sorbitol, polyethylene glycol, polyoxyethylene glycol, mannitol, xylitol, and other sugar alcohols. Sorbitol and glycerol (glycerin) are preferred.

Polishing agents or abrasives that are suitable in the toothpaste of this invention include finely divided water-insoluble powdered materials many of which are known to those skilled in the art. These materials have polishing activity without being overly abrasive. Examples include dicalcium phosphate, tricalcium phosphate, sodium metaphosphate, crystalline silica, colloidal silica, complex aluminosilicates, calcium carbonate, magnesium carbonate, magnesium phosphate, calcium pyrophosphate, bentonite, talc, calcium silicate, calcium aluminate, aluminum oxide, silica xerogels. A preferred abrasive is a silica based abrasive.

The surface active agents (detergents) that may be used in the toothpaste of this invention are those commonly used to emulsify or otherwise uniformly disperse toothpaste components. It is generally preferred that the detergent be anionic or nonionic or a mixture thereof. Suitable types of anionic detergents include sodium lauryl sulfate, fatty acid monoglyceride sulfates, fatty alkyl sulfates, higher alkyl aryl sulfonates, higher alkyl sulfoacetates, higher olefin sulfonates, higher aliphatic acylamides of lower aliphatic aminocarboxylic acids, higher alkyl poly-lower alkoxy (of 3 to 100 alkoxy groups) sulfates, and fatty acid soaps. Examples of these anionic detergents include sodium lauryl sulfate, sodium hydrogentated coconut oil fatty acids monoglyceride monosulfate, sodium N-lauroyl sarcoside, and sodium cocate. Suitable types of nonionic detergents include chains of lower alkyene oxides such as ethylene oxide and propylene oxide.

Additional materials that are optionally added include flavorings, enamel hardening agents, and antibacterial compounds. Examples of flavoring materials include the sweetener saccharin, essential oils such as spearmint, peppermint, wintergreen, eucalyptus, lemon and lime. Examples of hardening agents include sodium monofluorophosphate, sodium fluoride and stannous fluoride. Examples of antibacterials are sodium benzoate, triclosan, and methyl or ethyl parasept.

Toothpastes of this invention may be prepared as opaque or translucent. Without the addition of an opacifier the toothpastes have good transparency. Titanium dioxide is a preferred opacifier that may be added to provide an opaque toothpaste without otherwise affecting the physical attributes of the formulation.

Toothpaste formulations of the present invention may be prepared in a manner known to those skilled in the art. An example of a general procedure performed at ambient temperature is as follows. The binder is dispersed into sorbitol or glycerin with high speed stirring and the dispersion is stirred at that speed for 5 minutes. Water is added and the resulting gum slurry is stirred for an additional 15 minutes. Separately, a dry blended mixture is prepared from sodium saccharin and sodium benzoate. If sodium fluoride, sodium monofluorophosphate, titanium dioxide or any other salts are to be used, they are added to the mixture at this stage. The mixture is then dispersed into the gum slurry and stirred at low speed stirring for 10 minutes to form a gel. Color is added and mixed in by stirring for 5 minutes. The gel is then transferred to a Ross® Mixer. Silica is added and mixed for 15 minutes under partial vacuum (at least 720 mm Hg). Flavor is added and mixed for 10 minutes under full vacuum, then sodium lauryl sulfate is added and mixed for 15 minutes under full vacuum. At this point, a sample may be withdrawn for testing and the batch discharged for tube filling.

The following Examples illustrate but do not limit the invention.

EXAMPLES

Comparisons were made among a number of formulations with varying amounts of kappa carrageenan and CMC. To evaluate the effect of the binder on stringiness, Cuban values, and stability, components other than the kappa carrageenan and CMC binder were kept constant. Table 1 shows the ingredients that were kept constant in one set of comparisons.

TABLE 1

Components other than Binder

|  | Percent |
|---|---|
| Sorbitol 70% | 68.00 |
| Saccharin | 0.20 |
| Sodium benzoate | 0.20 |
| Silica (precipitated) | 7.00 |
| Silica (abrasive) | 11.00 |
| Flavor | 1.00 |
| Sodium lauryl sulfate | 2.00 |
| Water | 9.80–10.15 |

Table 2 illustrates some of the formulations containing the ingredients in Table 1 and varying amounts of kappa carrageenan and CMC.

TABLE 2

Representative Test Formulations

| Number | Kappa Carrageenan | CMC | Iota Carrageenan* | Xanthan |
|---|---|---|---|---|
| 1 | 0.38 | 0.23 | — | — |
| 2 | 0.32 | 0.13 | — | — |
| 3 | 0.30 | 0.15 | — | — |
| 4 | 0.34 | 0.21 | — | — |
| 5 | 0.31 | 0.19 | — | — |
| 6 | 0.50 | 0.30 | — | — |
| 7 | 0.30 | 0.20 | — | — |
| 8 | 0.31 | 0.29 | — | — |
| 9 | 0.25 | — | 0.05 | — |
| 10 | 0.20 | — | 0.10 | — |
| 11 | 0.15 | — | 0.15 | — |
| 12 | 0.10 | — | 0.20 | — |
| 13 | 0.15 | — | 0.20 | — |
| 14 | 0.20 | — | 0.20 | — |
| 15 | 0.20 | — | — | 0.50 |
| 16 | 0.40 | — | — | 0.40 |
| 17 | — | — | 0.45 | — |
| 18 | — | — | 0.35 | — |
| 19 | — | 0.50 | — | — |
| 20 | — | 0.70 | — | — |
| 21 | — | — | — | 0.50 |
| 22 | — | — | — | 0.75 |

*Iota carrageenan content is from about 90% to 100%.
Formulations prepared with iota carrageenan contain 0.03% potassium chloride.

Test Results

For each of the formulations prepared, stringiness, Cuban values, and physical stability were measured.

The stringiness of the formulation was measured using a texture analyzer. The texture analyzer is fitted with a plunger that moves downward and touches a sample of toothpaste. The plunger remains on the sample for a stipulated time and then starts moving upward bringing with it a string of toothpaste. After the plunger reaches a particular height or distance on its upward ascent, the toothpaste string will break. The test is stopped as soon as the string breaks and the distance travelled in millimeters by the plunger is the measure of stringiness. The following is a detailed procedure that was used to measure stringiness for this invention. A two gram sample of toothpaste was placed at the center of the lower plate of a texture analyzer. The force of the plunger was set at 200 g, and the pretest speed of the plunger was set at 1 mm/sec. Pretest speed is the speed that the plunger will travel down before starting the test. The sample holding time for the plunger was set at two seconds. This allows the plunger to touch the sample on the holding plate and remain there for two seconds before traveling upward. The post test time was set at 1 mm/sec. This is the speed at which the plunger travels upward. The test was stopped as soon as the string broke and the distance travelled in millimeters by the plunger was measured.

Cuban test values are directly related to the viscosity of the toothpaste. In the Cuban test (also termed the "Rack" test), the paste is squeezed from a tube through a fixed orifice across a grid of parallel rods, increasingly spaced apart. The test results are expressed as the greatest space number (numbers are from 1–12) which represents the longest distance between rods that support the dentrifice ribbon without having it break. The rack is about 300 millimeters (mm) long and about 100 mm wide. The stainless steel rods are spaced at increasing distances apart starting at 3 mm between rods 1 and 2 (space number 1) and the distance between rods increases by 3 mm from rod to rod. Thus the distance between rods 2 and 3 is 6 mm, and the distance between the twelth and thirteenth rod (space number 12) is 39 mm. Ratings of 1–2 and 9–12 are not acceptable, 3 and 8 are acceptable, 4–7 are good.

Stability tests were conducted by filling tubes with the sample paste. The tubes were capped and stored flat for 12 weeks at room temperature and at 50° C. After the twelve week exposure, a toothpaste ribbon of about 5 cm in length was squeezed from the tube and examined. The tubes were then slit open and the contents evaluated for flavor and phase separation (syneresis). The separation of the flavoring and water phase at the tip of the toothpaste tube may be noted as "wet cap". Flavor separation was rated as 1=slight, 2=moderate and 3=severe. Stability was rated as "not ok", "ok", and "good". To be rated "not ok," the sample readily exhibited some undesirable properties such as flavor separation, syneresis, being very hard in the tube, or having unacceptable Cuban values. To be rated "ok," the sample did not separate but could be somewhat grainy and lacking in good sheen. To be rated "good," the sample exhibited no separation of any sort and the sample was superior in subtle details such as fine texture or not grainy and had superior sheen or gloss. Table 3 shows the results of the Cuban and stability testing for the formulations described above in Tables 1 and 2.

TABLE 3

Test Results

| Number | Cuban value | Stability RT | Stability 50° C. |
|---|---|---|---|
| 1 | 5 | good | good |
| 2 | 5 | good | good |
| 3 | 3 | good | good |
| 4 | 5 | ok | ok |
| 5 | 5 | ok | ok |
| 6 | 9 | thick | thick |
| 7 | 5 | slighty thick | slighty thick |
| 8 | 5 | ok | ok |
| 9 | 10 | ok | flavor sep. |
| 10 | 9 | ok | flavor sep. |
| 11 | 9 | ok | flavor sep. |
| 12 | 5 | ok | flavor sep. |
| 13 | 8 | thick | ok |
| 14 | 9 | thick | flavor sep. |
| 15 | 3 | ok | ok |
| 16 | 4 | ok | ok |

Entries 1–8 in Table 3 are kappa carrageenan/CMC formulations where the ratio of kappa carrageenan to CMC is in the range of 52:48 to 71:29. As can be seen from Table 3, the Cuban values for the kappa carrageenan/CMC formulations (entries 1–8) are good when the percent by weight concentration of kappa carrageenan was greater than 0.30% and less than 0.50%. At the higher concentration of kappa carrageenan, thickening also becomes a problem over the extended time period.

Entries 9–14 of Table 3 are representative of the attempts to prepare a suitable binder by mixing kappa and iota carrageenan. As can be seen from the Cuban values and/or the stability results, these formulations were generally unacceptable. Entry 15 of Table 3 is representative of an unsuccessful attempt to prepare a suitable binder by mixing kappa carrageenan and xanthan.

In addition to providing a kappa carrageenan-based gel toothpaste having good viscosity and stability, a further objective was to provide such a toothpaste that is also non-stringy. As used herein, the term "non-stringy" refers to a toothpaste having low stringiness (below about 20 mm). It was found that certain gel toothpastes comprised of a binder containing kappa carrageenan and CMC exhibited surprisingly low stringiness. To provide a toothpaste having low stringiness, a preferred percent by weight concentration of binder is in the range of about 0.45 to 0.61%. Within this range, a preferred ratio of kappa carrageenan to CMC is in the range of about 62:38 to 71:29. Table 4 shows how some representative toothpastes of this invention compare with other toothpaste formulations, including some commercial brands which are widely used. The formulations for entries 1–22 are described above in Tables 1 and 2.

TABLE 4

Comparison of Stringiness

| Number | Stringiness (mm) |
|---|---|
| 1 | 15.0 |
| 2 | 11.9 |
| 17 | 22.7 |
| 18 | 22.9 |
| 19 | 20.2 |
| 20 | 26.1 |
| 21 | 19.4 |
| 22 | 22.7 |
| Brand A | 18.7 |
| Brand B | 19.2 |
| Brand C | 18.2 |
| Brand D | 13.6 |

The toothpastes of this invention (represented in Table 4 by entries 1 and 2) have very low stringiness. The stringiness of these toothpastes is substantially lower than three of the four commercial toothpastes tested and certain toothpastes of this invention are significantly less stringy than the best commercial product tested. The low stringiness was achieved with formulations that employed relatively low amounts of kappa carrageenan in gels that exhibited good consistency and stability.

We claim:

1. An improved toothpaste composition having reduced stringiness, low levels of syneresis and high stability against hardening on standing, wherein said composition comprises an orally acceptable aqueous vehicle, a polishing agent, a surface active agent and a binder, in which (a) the binder consists of kappa carrageenan and carboxymethylcellulose, the percent by weight concentration of binder is in the range of about 0.45% to about 0.65%, the ratio of kappa carrageenan to carboxymethylcellulose is in the range of about 60:40 to 75:25, and (b) the abrasive is a silica-based abrasive and (c) the percent by weight concentration of kappa carrageenan is in the range of about 0.30% to 0.50% and the percent by weight concentration of carboxymethylcellulose is in the range of about 0.13% to 0.23%.

2. The composition of claim 1 in which the concentration of kappa carrageenan is in the range of about 0.32 to about 0.38% and the concentration of carboxymethylcellulose is in the range of about 0.13 to 0.23%.

3. The composition of claim 1 in which the composition has a Cuban value in the range of about 4 to 7.

4. The composition of claim 2 in which the composition has a Cuban value in the range of about 4 to 7.

5. The composition of claim 1 further comprising a humectant selected from the group consisting of sorbitol, glycerin, and mixtures thereof.

6. The composition of claim 2 further comprising a humectant selected from the group consisting of sorbitol, glycerin, and mixtures thereof.

7. The composition of claim 1 further comprising a humectant selected from the group consisting of sorbitol, glycerin, and mixtures thereof, and wherein the composition has a Cuban value in the range of about 4 to about 7.

8. The composition of claim 2 further comprising a humectant selected from the group consisting of sorbitol, glycerin, and mixtures thereof, and wherein the composition has a Cuban value in the range of about 4 to about 7.

* * * * *

UNITED STATES PATENT AND TRADEMARK OFFICE
CERTIFICATE OF CORRECTION

PATENT NO. : 6,162,418
DATED : December 19, 2000
INVENTOR(S) : Vinayak Bhalchandra Randive et al.

It is certified that error appears in the above-identified patent and that said Letters Patent is hereby corrected as shown below:

<u>Column 8,</u>
Line 13, replace "consists of" with -- consists essentially of --.

Signed and Sealed this

Fourteenth Day of May, 2002

Attest:

JAMES E. ROGAN
Attesting Officer     Director of the United States Patent and Trademark Office